United States Patent [19]

Holden

[11] Patent Number: 4,877,320

[45] Date of Patent: Oct. 31, 1989

[54] EYE-SHIELDING GLASSES

[76] Inventor: W. Bruce Holden, 500 Cohasset Rd., Ste. 34, Chico, Calif. 95926

[21] Appl. No.: 252,541

[22] Filed: Oct. 3, 1988

[51] Int. Cl.⁴ .................. G02C 7/10; G02C 11/02; G02C 11/08
[52] U.S. Cl. .................................. 351/44; 351/52; 351/62
[58] Field of Search .............. 351/43, 44, 45, 62, 351/51, 52, 111

[56]  References Cited
U.S. PATENT DOCUMENTS

| | | |
|---|---|---|
| 294,833 | 3/1988 | Holden . |
| 2,296,634 | 10/1941 | Fink . |
| 2,596,572 | 5/1952 | Lindbloom ........................ 351/52 |
| 3,038,375 | 3/1962 | Gansz ............................... 351/43 |
| 3,497,294 | 2/1970 | Volk ................................. 351/62 |
| 3,526,449 | 9/1970 | Bolle et al. . |
| 4,515,448 | 5/1985 | Tackles . |
| 4,741,611 | 5/1988 | Burns . |

FOREIGN PATENT DOCUMENTS 868.552  9/1940  France .

OTHER PUBLICATIONS

"Combat Glasses", Sports Illustrated, 3/12/79.

Primary Examiner—Rodney B. Bovernick

[57] ABSTRACT

Eye-shielding glasses contoured to fit and completely cover the human eye area with a one-piece curved lens section is provided with hinge-attached, removable temples. The lens section has a widened overhanging top rim and a narrowed bottom rim formed centrally into an upwardly curved nose rest. The removable temples are pin-hinged inside of side shield hinge housings at both shorter ends of the one-piece lens section. At the hinge end, the temples widen into eye area protecting webbed sides. Both the web sections and the temples are removable and style changes can be accomplished by changing the web sections or the temples. To prevent fogging, vent slits are opened in the web sections partly covered by debris deflectors. In special sports glasses, the top rim is vented in debris deflecting projections and float attachments are provided by snap-in replacement web members and by a top-fitting snap-on tube section. The eye-shielding glasses are foldable for storage and a special nose piece is provided to achieve a more comfortable fitting for various sized human nose shapes.

16 Claims, 4 Drawing Sheets

EYE-SHIELDING GLASSES

CROSS-REFERENCE TO RELATED APPLICATIONS

The invention described herein constitutes new operational features and improvements over my sunglasses design illustrated in patent number Des. 294,833, issued Mar. 22, 1988.

BACKGROUND OF THE INVENTION

1. Field of the Invention

This invention relates to eye glasses in general and more specifically to protective sunglasses and safety glasses that can be worn alone or over prescription lenses. The present invention is particularly directed towards eye-shielding glasses having exchangeable features and the glasses curved and rimmed to contour with the wearer's face, completely enclosing the eye area. Well made, light weight, wraparound sunglasses in the genre of the present invention can provide an exceptionally comfortable and secure fit while filtering light and deflecting debris from all angles.

2. Description of the Prior Art

Conventional non-prescriptive sunglasses are traditionally structured with spherical lenses which do not have overhanging top and bottom rims and widened side arms designed to completely enclose the eye area. Sunlight and flying debris can enter the open side or top portion of those glasses and interfere with the wearer's vision and endanger the eye. The majority of traditional sunglasses including those seen in past art patented devices are generally not well suited for sports activities because of fragile structure. Sunglasses used for sports should remain secure during vigorous activities. Sports glasses should be sturdy enough to withstand a moderate degree of impact without breaking or without concentrating the major force of the impact directly on the bridge of the nose. To prevent reduced vision because of internal steaming, a method of ventilating the eye area of protective glasses is essential. Wraparound protective sunglasses need to be foldable for non-use portability and should be made in a manner that replacing temples for size adjustment is a simple procedure. Protective glasses and sunglasses seen in the past art patents do not seem to have approached these problems. Existing sunglasses and most safety glasses are not comfortably worn over prescription glasses and most do not provide ventilated peripheral protection from light and the danger of debris entering the eye area. These shortcomings are obvious in devices for the purpose seen in past art patents.

Patents representing devices considered most pertinent to my invention included the following:

1. U.S. Pat. No. 2,296,634, issued to Fink on Sept. 22, 1942, discloses an eye-shield designed to completely cover the eye area.

2. Bolle et al was granted U.S. Pat. No. 3,526,449, on Nov. 9, 1967, for one-piece sunglasses having concavo-convex shaped temple portions and inwardly projecting upper and lower lips.

3. Tackles was granted U.S. Pat. No. 4,515,448, on May 7, 1985, for sunglasses having removable frusto conically shaped lenses designed to cover the eye area.

4. On May 3, 1988, Burns was issued U.S. Pat. No. 4,741,611, for eyeglasses adapted for sports and protective use.

None of the examined patents seem to have provided glasses or sunglasses with protective features and ventilation, with the glasses structured to be worn alone or over prescription glasses. Convexly shaped lenses having a severe degree of curvature appear to be the main offering. Upper and lower rims are seen which appear to interfere with the upper and lower rims of corrective lenses and spoil a proper fit. Although some devices were foldable, ventilation and eye area protection were not adequately provided and no easily removable and replaceable temples for size adjustment and design changes were disclosed. The Burns device appears to have a lens with less of a curvature, but the nosepiece shown in the drawings would interfere with the nosepiece on most corrective glasses, making simultaneous usage impossible.

Fink, Burns, and Tackles show devices using pins, screws, or elastic bands for hinging. The application of an additional part in the assembly process of any item increases production costs. Pins and screws used for eyeglass hinges are also notoriously known for becoming loose and subsequently lost. The screw apertures are also frequently stripped causing an especially aggravating repair problem costly to the wearer. Elastic straps shown in one embodiment of the Fink device and the thin wire temples shown in the Tackles patent do not adequately protect a wearer's eyes and do not prevent light or debris from entering the sides of the glasses. A strap or wire hinging method also provides a less secure attachment means. Although a French patent issued to L. & G. Bolle, U.S. Pat. No. 868,552, shows a wire insert hinge method for plastic sunglasses, a U.S. Pat. No. 3,526,449, showing a similar name, M. Bolle et al, describes one-piece glasses having no temple hinging means. Safety or sunglasses which do not fold are inconvenient for storing, especially when the majority of storage cases for glasses are designed for folding glasses. Lens fogging because of no eye area ventilation appears to be an obvious problem in most wraparound sunglasses.

To my knowledge, the foregoing patents represented devices most pertinent to my invention. As will be seen in the following specification, my invention overcomes the mentioned disadvantages seen in past art devices, and provides new and useful benefits as well.

SUMMARY OF THE INVENTION

In practicing my invention, I have combined sunglasses and safety glasses in a single foldable structure. Using modern space-age materials and methods in my eye-shielding glasses, I provide a sunglasses-safety glasses combination fabricated to be practically indestructible and which can be worn alone or comfortably over prescription glasses of most configurations. For style and contoured fitting of the human eye area, my glasses are combined in a one-piece curved lens section with overhanging top and bottom rims and widened temple-connecting side shields. The widened side shields together with the overhanging rims completely encircle the lens area controlling light passage and eliminating dust or flying debris from directly entering the eye area. In a particular sports embodiment of the invention, the overhanging top rim has an alignment of open air vents formed in the material frontwardly protected by a projection with the openings angled back towards a protective vertical rim edge at the wearer's forehead. This upward venting prevents accumulation of moisture in the eye area and reduces lens fogging. My glasses are equipped with removable temples. The temples are vertically widened at the eye area and pin hinged for easy attachment and detachment inside widened side shield hinge housings at each end of the one-piece curved lens section. A vertical temple wing fitting inside the pin housing and upper and lower pin hinge connections provide secure attachment and additional side-eye protection. At the hinge end, the temples in my glasses are widened into a triangular frame supporting a webbed center. The webbed center was vertical ventilating slits aligned frontwardly by debris deflecting partial coverings to protect the wearer's eye area. The temples are designer logo applicable in that the temples can be easily exchanged with temples having a variety of designs in the ventilated webbed area. The webbed area in the special sports glasses is configured triangularly and has removable snap-in members. These snap-in members include hollowed air entrapping attachments so the glasses will float if dropped during water sports. A tubular float can also be snapped to the top of the glasses for additional buoyancy when needed. A variety of snap-in web designs is available to change the appearance of the glasses at the manufacturer's or user's discretion. The snap-in web replacements are useful for designer logos and for advertising in general. The exchangeable temples also provide a temple adjustment means for differences in human head sizes. Although my eye-shielding glasses are designed to be comfortably and securely worn over corrective eyeglasses, the lens section is well suited for corrective lansing with and without sun protective coloring. An optional snap-on nose piece is provided to fit the formed nose rest designed into the glasses. The snap-on nose piece is available to make the glasses a more comfortable fit for persons with different shaped noses. The glasses are designed to be manufactured of an extremely durable, high impact and mar resistant transparent plastic. When used as safety glasses, the plastic is left clear or lightly tinted. When used for sunglasses, the lens portion is specially treated to eliminate one-hundred percent of ultra violet light and thirty percent of infrared light. The lens frame and temples normally have sun ray protective coloring. With corrective lenses ground in the lens section, my eye-shielding glasses can be worn in place of regular corrective glasses.

The eye-shielding glasses of this invention provides safety glasses useful for sports, motorcycle riding, mechanical and electrical work, and virtually any application where conventional safety goggles or sunglasses are now used. For sports enthusiasts, my glasses supply both sunglasses and safety glasses, have ventilating features to prevent fogging, and have attachable features to provide floatation. For the design conscious individual, my changeable temples with the widened webbed members both fixed and snap-in at the attachment ends, providing a designer logo labeling surface.

Although the lens section of my device is structured in one size to fit all, limited adjustments are possible without changing attachments by applications of heat and force and by manually bending the ear hook end of the temple section to the desired form.

Therefore, it is a primary object of my invention to provide sunglasses and safety glasses combined in a single pair of eye-shielding glasses having eye area ventilation and which can be worn over corrective glasses.

Another object of my invention is to provide a sunglasses and safety glasses combination with features to prevent fogging and with peripheral protection against light and flying debris from entering the eye area.

A further object of the invention is to provide sunglasses and safety glasses in a combined unit having webbed front foldable temples with the temples removable for size adjustment and for replacement by designer endorsed temples.

A still further object of my invention is to provide wraparound sunglasses for practical and sports use having snap-on attachments providing design changes in the appearance of the glasses and a floatation device for the glasses if lost overboard during water sports.

Other objects and advantages of my invention will become apparent with a reading of the remaining specification and comparing numbered parts described with similarly numbered parts shown in the accompanying drawings.

DESCRIPTION OF THE PREFERRED EMBODIMENTS

Figure 1:
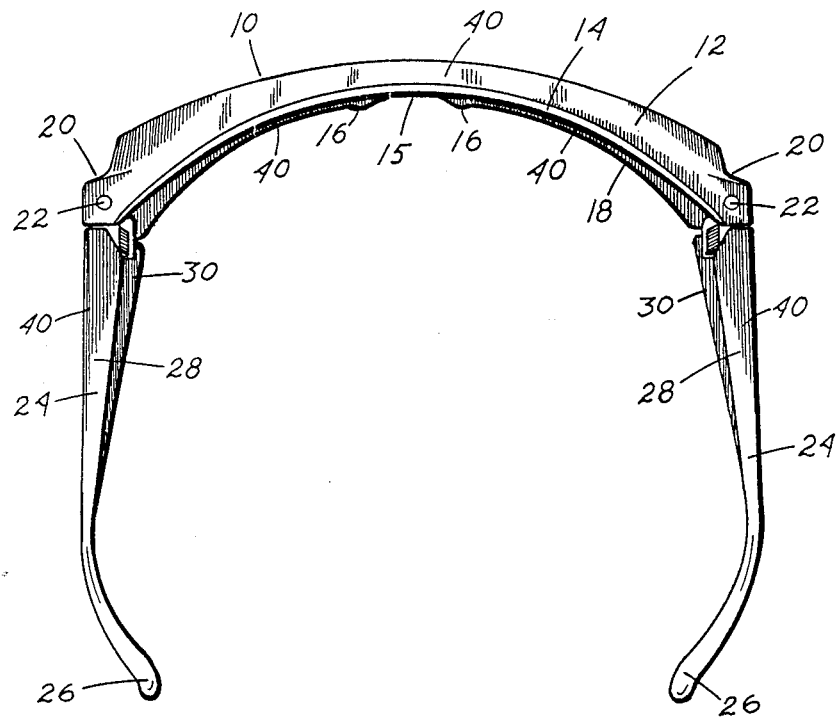
FIG. 1 is a top plan view of the eye-shielding glasses.

Referring now to the drawings where the eye-shielding glasses constituting the invention are illustrated in various attitudes. In FIG. 1, one-piece curved lens section 10 is shown in a top plan view with temples 24 attached. Top rim 12 frames the upper edge of one-piece curved lens section 10 paralleling the upper inside concave curve of one-piece curved lens section 10. Vertical top rim edge 14, shown horizontally positioned in FIG. 1, is an upwardly right angled curved pad-like lip edging along the inside of top rim 12. The tops of side shield hinge housing 20 can be seen in FIG. 1, one at each end of one-piece curved lens section 10, with two top pin hinge apertures 22 showing. The inward curvature of ear hooks 26, the inward (downward in the illustration) extending lower ends of formed nose rest 16, and a partial view of narrowed bottom rim 18 are shown in FIG. 1. One-piece curved lens section 10, temples 24, and other parts herein described are designed to be manufactured of an extremely durable, high impact and mar resistant transparent plastic such as polycarbonate as the material of choice.

Figure 2:
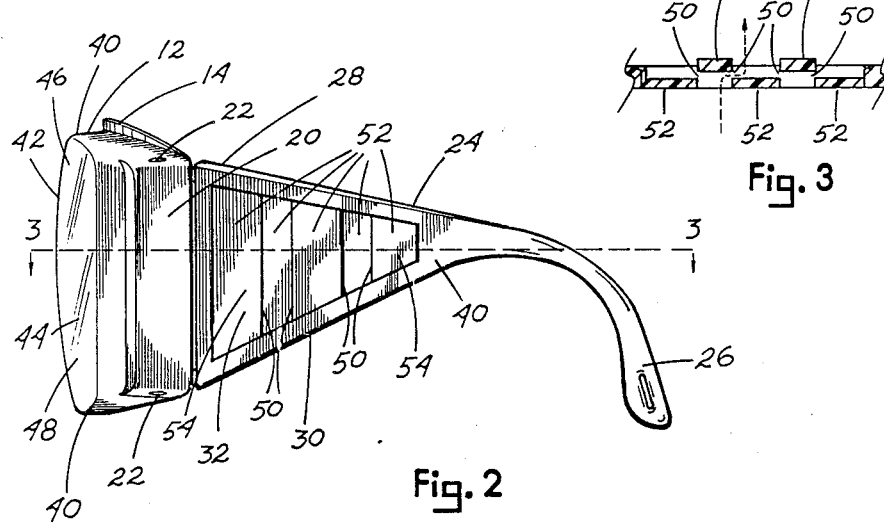
FIG. 2 is a left side view thereof; the right side being essentially identical in reverse.
Figure 4:
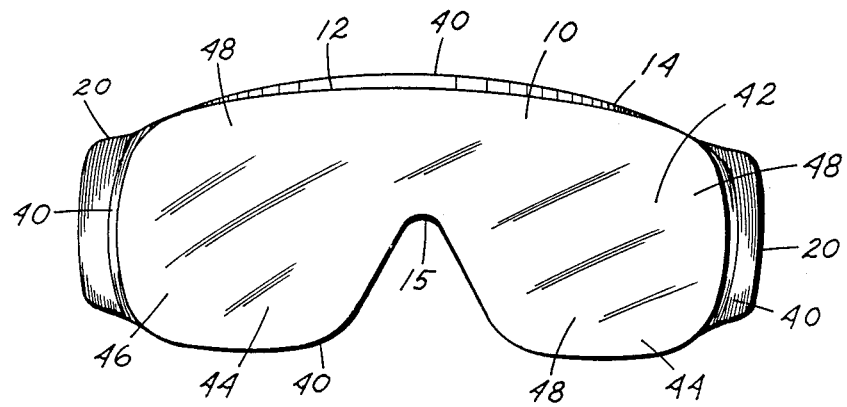
FIG. 4 is a frontal view of the eye-shielding glasses.
Figure 7:
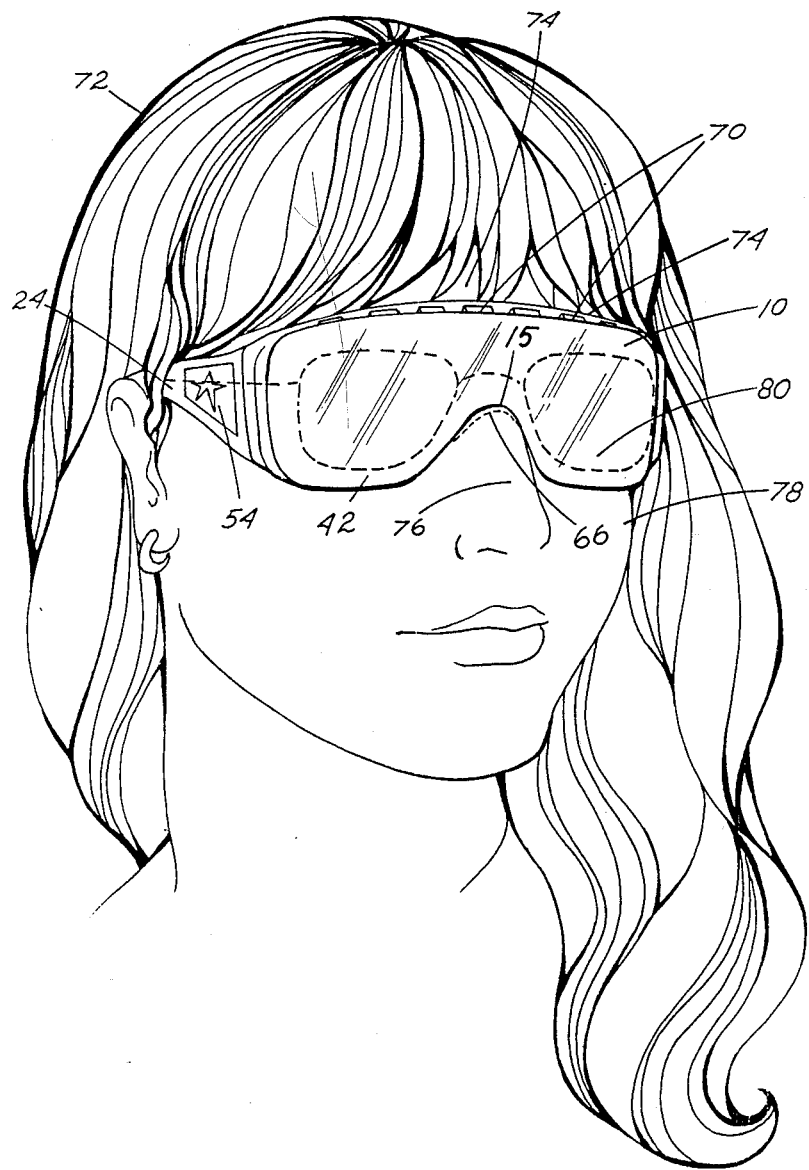
FIG. 7 is an in use view illustrating the eye-shielding glasses being worn over conventional corrective lenses.

In FIG. 2 and FIG. 4, the eye-shielding glasses of this invention is illustrated in the normal use attitude. In FIG. 4, one-piece curved lens section 10 is vertically positioned longitudinally horizontal and is centrally intersected downwardly by upwardly semicircular bridge 15. FIG. 2 is a left side view of one-piece curved lens section 10 with temple 24 attached. It is noted that a right side view would be essentially identical in reverse. In FIG. 2, top rim 12 is a horizontal continuation of one-piece curved lens section 10 having the upper edge turned up into lip-like vertical top rim edge 14. Vertical top rim edge 14 is a pad-like edging designed to contour with the forehead 74 of wearer 72. See FIG. 7. Narrowed bottom rim 18 is the lower turned in edging of one-piece curved lens section 10 sized to contour with cheek 78 of wearer 72. These parts are mainly shown in FIGS. 2, 4, and 5 with FIG. 7 illustrating the eye-shielding glasses in use.

Figure 3:
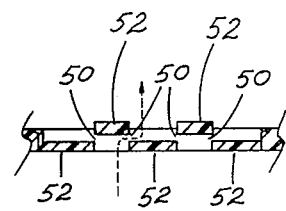
FIG. 3 is a top cross sectional view of the ventilated web section of FIG. 2.
Figure 5:
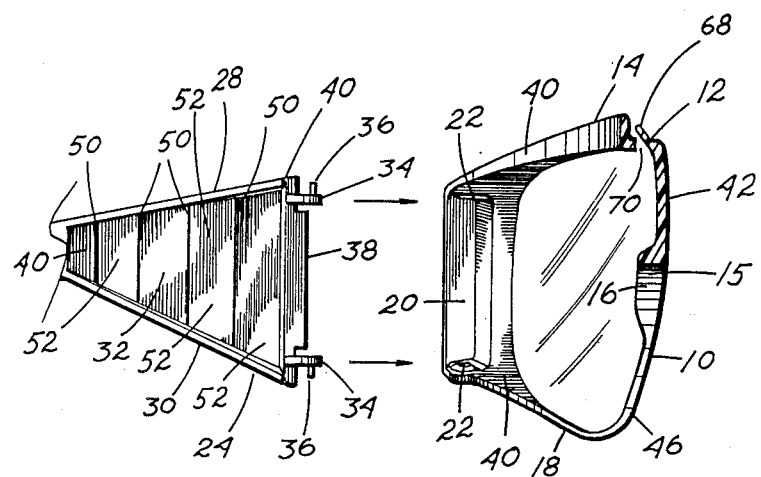
FIG. 5 is an unassembled interior left side view illustrating the lens portion transacted at the bridge of the nose and the forward portion of the removable temple with frontal webbing.

In the side view at FIG. 2, side shield hinge housing 20, which is a unique and important formed continuation of one-piece curved lens section 10, is shown with temple 24 attached. Pin hinge apertures 22 are shown in the top and bottom sections of side shield hinge housing 20. Temple 24 terminates at the small end into ear hook 26. At the attachment end, temple 24 widens into angled temple upper web frame 28 and angled temple lower web frame 30 with the section between the two angled frames filled by temple side webbing 32. Temple side webbing 32 fitted closely to side shield hinge housing 20 with vertical temple wing 38 extending inside side shield hinge housing 20 provides protection to the eye area from both sun rays and the entrance of debris. Ventilating slits 50 spaced vertically in temple side webbing 32 are partially covered by slit deflector coverings 52 raised to deflect debris from entering the eye area. FIG. 3 illustrates positioning of deflector coverings 52 in relationship to ventilating slits 50. Ventilating slits 50 allow air passage into the eye area to prevent fogging of safety lens 46. Temple side webbing 32 presents an ideal area to be used for a company name, an advertisement, and as designer labeling area 54. As shown in FIG. 5, changes can be accomplished by replacing temple 24 with an alternate temple 24 embellished as desired in the temple side webbing 32 area. Replacing temple 24 also serves a second purpose in that a longer or shorter temple 24 can be supplied to adjusted for differences in human head sizes. Pins 36 which attach temples 24 to side shield hinge housing 20 on one-piece curved lens section 10 pop into pin hinge apertures 22 providing secure hinged attachment for temples 24. Compressing pin hinge support members 34 towards each other allows temples 24 to be easily removed and replaced.

Figure 6:
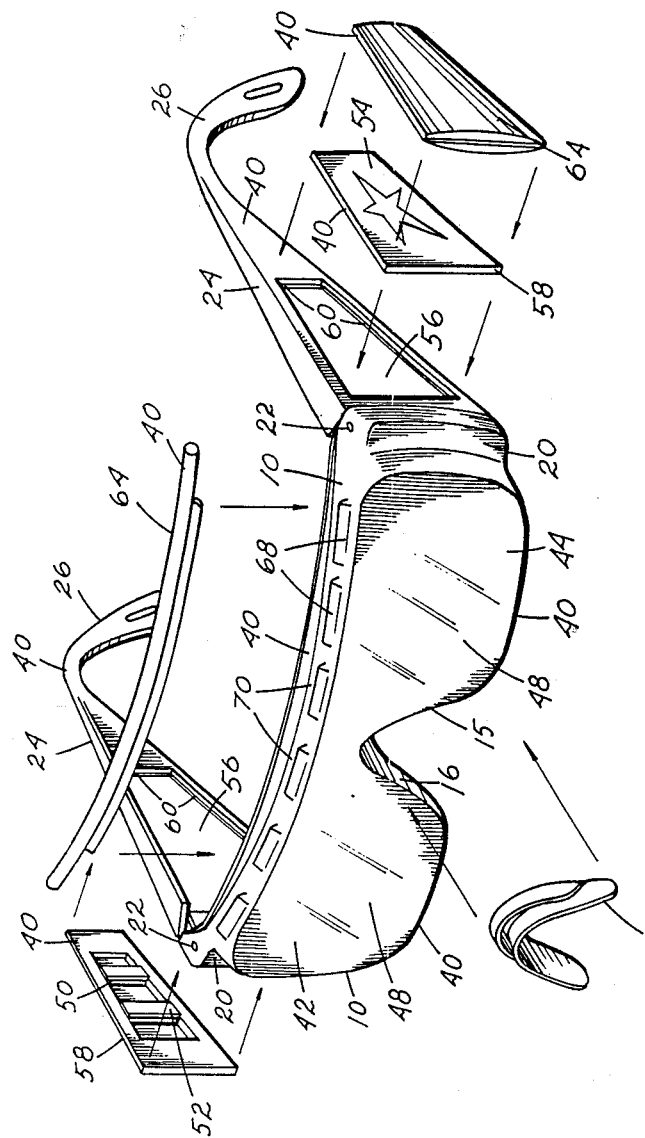
FIG. 6 is a perspective drawing of the assembled glasses with the attachable parts illustrated exploded in position for attachment.

In a special sports embodiment illustrated in FIG. 6, temple side webbing 32 is replaceable and when removed a temple snap-in receiver aperture 56 edged on the inside by stops 60 is available. Snap-in web member 58 embellished with a company name, advertising, or a designer designation in designer labeling area 54 fits into snap-in receiver aperture 56 against stops 60. Snap-in web member 58 is insertable because of pliability in the material and is retained by resiliency in the same material and by inwardly angled corresponding edges along the frame of temple snap-in receiver aperture 56 and snap-in web member 58. Inserts can include various snap-in web members 58 and snap-in web float member 62. Snap-in web float member 62 is a sealed member having two somewhat convexed outer walls with air trapped in the concave formed chamber between the two walls. When two snap-in web float members 62 are snapped into temple snap-in receiver aperture 56 sufficient buoyancy is produced to provide floatation for the present invention. For additional flotation support, a snap-on tubular float member 64, a hollow air filled tubing, is provided for attachment to the top of one-piece curved lens section 10 by snap-attachment to top rim 12 around vertical top rim edge 14. Either snap-on tubular float member 64 or two snap-in web float members 62 provides sufficient buoyancy when used along to prevent the glasses of the present invention from sinking in water. For sports use, this embodiment is arranged with an alignment of upper vents 70 opened along top rim 12. Upper vents 70 allow moisture to escape from the eye area and help prevent fogging of one-piece curved lens section 10. Upper vents 70 are opened towards vertical top rim edge 14 somewhat angled upwardly in the back sides of upper vent projections 68. Upper vent projections 68 are hood-like coverings formed upwardly front to rear in the surface of top rim 12 to prevent direct access of wind or debris into upper vents 70 from the direction wearer 72 is facing or moving. See FIG. 7. To better fit different nose sizes and shapes, a snap-on auxiliary nose piece 66 is provided which fits over formed nose rest 16 and somewhat lowers and narrows the nose area.

One-piece curved lens section 10 and the two temples 24 are normally manufactured of plastic with sun ray resistant coloring 40 in the materials. However, the materials used to fabricate the one-piece curved lens section 10, the two temples 24, and other parts described are not limited to any particular material or coloring so long as materials used and coloring applied produces a satisfactory end product equivalent to plastic heretofore described as the material of choice. Sunglasses and safety lens colored 42, safety lens uncolored 44, safety lens 46, and safety prescription corrected lens 48 can all be structured into various forms of the finished product constituting this invention.

In use, as shown in FIG. 7, the assemblage of one-piece curved lens section 10 and temples 24 adequate cover corrective glasses 80 worn by wearer 72. Formed nose rest 16 covers the bridge of the nose 76 of wearer 72 and the use of snap-on auxiliary nose piece 66 is illustrated by dotted lines. Vertical top rim edge 14 rests against the forehead 74 of wearer 72 and narrow bottom rim 18 follows the contour of wearer 72 cheeks 78. One-piece curved lens section 10 in cooperation with temples 24 provide wearer 72 with a complete covering of the eye area by safety lens 46 or sunglasses and safety lens colored 42.

Although I have described the principal embodiments of my invention with considerable details in the foregoing specification, it is to be understood that modifications in the design and changes in the structure may be practiced which do not depart from the intended scope of the appended claims.

What I claim as my invention is:

1. In eye-shielding glasses of a type having a pair of transparent lenses formed in a one-piece curved lens section narrowed centrally by a bridge opening and retained to a human face by ear hooking temples, improved glasses comprising:

circuitous framing edgewise along said lens section being a molded continuation thereof interfacing a concave surface side of said lens section, said framing being a wide horizontal strip along the upper edge of said lens section ending longitudinally flanged upwardly into a short vertical lip, said framing being a narrow horizontal strip along the lower edge of said lens section widened into a frame for a nose rest along a semicircular bridge, said framing forming transversely along both shorter ends of said lens section into side shielding hinge housing having temple attachment apertures upwardly downwardly inside said side shielding hinge housing;

two temples each having ear hooks at distal ends thereof and oppositely widened into framed air vent web sections adjacent insert end members affixed with upwardly and downwardly positioned hinging attachment pins, said temples attaching inside said side shielding hinge housing and being and being snap-in and removable for replacement by various temples having a variety of designs in said framed air vent web section.

2. The improved glasses of claim 1 wherein said one-piece curved lens section, said molded frame, said temples and parts thereof being fabricated from durable, high impact and mar resistant plastic.

3. The improved glasses of claim 1 wherein in said glasses curtail sun ray passage through the lens section, said circuitous framing, and said temples having sun ray resistant coloring manufactured into the materials.

4. The improved glasses of claim 1 wherein said one-piece curved lens section of said glasses being provided with prescription lenses.

5. The improved glasses of claim 1 wherein snap-on auxiliary nose pieces fitting said lens section widened somewhat into a frame for a nose rest are provided in sizes and shapes selectable by a wearer.

6. The improved glasses of claim 1 wherein a sealed hollow auxiliary flotation tube is contoured to the shaped of said wide horizontal strip framing along said upper edge of said lens section ending longitudinally flanged upwardly into a short vertical lip with said flotation tube arranged to fit over and snap onto said vertical lip and said framing.

7. In eye-shielding glasses of a type having a pair of transparent lenses formed in a one-piece curved lens section narrowed centrally by a bridge opening and retained to a human face by ear hooking temples, improved glasses comprising:

circuitous framing edgewise along said lens section being a molded continuation thereof interfacing a concave surface side of said lens section, said framing being a wide horizontal strip along the upper edge of said lens section ending longitudinally flanged upwardly into a short vertical lip, said framing being a narrow horizontal strip along the lower edge of said lens section widened into a frame for a nose rest along a semicircular bridge, said framing forming transversely along both shorter ends of said lens section into side shielding hinge housing having temple attachment apertures upwardly and downwardly inside said side shielding hinge housing;

two temples each having ear hooks at distal ends thereof and oppositely widened and formed into frames holding snap-in removable insert panels with said frames adjacent insert end members affixed with upwardly and downwardly positioned hinging attachment pin, said temples attaching inside said side shielding hinge housing and being snap-in and removable for replacement.

8. The improved glasses of claim 7 wherein said one-piece curved lens section, said molded frame, said temples and parts thereof being fabricated from durable, high impact and mar resistant plastic.

9. The improved glasses of claim 7 wherein in said glasses curtail sun ray passage through lens section, said circuitous framing, and said temples having sun ray resistant coloring manufactured into the materials.

10. The improved glasses of claim 7 wherein said one-piece curved lens section of said glasses being provided with prescription lenses.

11. The improved glasses of claim 7 wherein snap-on auxiliary nose pieces fitting said lens section widened somewhat into a frame for a nose rest are provided in sizes and shapes selectable by a wearer.

12. The improved glasses of claim 7 wherein a sealed hollow auxiliary flotation tube is contoured to the shaped of said wide horizontal strip framing along said upper edge of said lens section ending longitudinally flanged upwardly into a short vertical lip with said flotation tube arranged to fit over and snap onto said vertical lip and said framing.

13. The improved glasses of claim 7 wherein said snap-in removable insert panels are exchangeable with like panels affixed with surface designs.

14. The improved glasses of claim 7 wherein said snap-in removable inserts panels are exchangeable with like panels having ventilation openings cut through said panels with said openings cut in a manner to produce variations in the design of different panels.

15. The improved glasses of claim 7 wherein said snap-in removable insert panels are provided in replacement panels sealed along the edges and having hollow centers with said replacement panels providing flotation assistance for said glasses.

16. The improved glasses of claim 7 wherein said wide strip having an upwardly flanged vertical lip with said wide strip horizontally framing said upper edge of said lens section having vents cut in angular vent projections spaced along said wide strip with said vents opened towards said upwardly flanged vertical lip.

* * * * *